United States Patent [19]

Schickaneder et al.

[11] Patent Number: 5,047,431
[45] Date of Patent: Sep. 10, 1991

[54] 1,1,2-TRIPHENYLBUT-1-ENE DERIVATIVES

[75] Inventors: Helmut Schickaneder, Poing; Roland Löser, Feldafing; Helmut Grill, Vaterstetten, all of Fed. Rep. of Germany

[73] Assignee: Klinge Pharma GmbH & Co., Munich, Fed. Rep. of Germany

[21] Appl. No.: 523,266

[22] Filed: May 14, 1990

Related U.S. Application Data

[63] Continuation of Ser. No. 930,015, Nov. 5, 1986, abandoned, which is a continuation of Ser. No. 800,356, Nov. 21, 1985, abandoned, which is a continuation of Ser. No. 328,723, Dec. 8, 1981, abandoned.

[30] Foreign Application Priority Data

Dec. 11, 1980 [DE] Fed. Rep. of Germany ....... 3046719

[51] Int. Cl.$^5$ .................. A61K 31/135; C07C 217/20
[52] U.S. Cl. .................................... 514/648; 514/874; 564/324
[58] Field of Search ................. 564/324; 514/648, 874

[56] References Cited

U.S. PATENT DOCUMENTS

| | | | |
|---|---|---|---|
| 3,288,806 | 11/1966 | De Wald | 564/324 X |
| 3,341,537 | 9/1967 | Richardson | 564/324 X |
| 4,198,435 | 4/1980 | Richardson | 564/324 X |
| 4,206,234 | 6/1980 | Richardson | 424/330 |
| 4,536,516 | 8/1985 | Harper et al. | 564/324 X |
| 4,623,660 | 11/1986 | Richardson | 564/324 X |

FOREIGN PATENT DOCUMENTS

| | | | |
|---|---|---|---|
| 1029221 | 5/1966 | United Kingdom | 564/324 |
| 1064629 | 4/1967 | United Kingdom | 564/324 |

OTHER PUBLICATIONS

March, Advanced Organic Chemistry, 2nd Ed., McGraw-Hill Book Company, (1977), pp. 99–101 and 113 to 115.
Wagner et al., "Synthetic Organic Chemistry", pp. 171–172 (1963).

Primary Examiner—Richard L. Raymond
Attorney, Agent, or Firm—Burns, Doane, Swecker & Mathis

[57] ABSTRACT

Novel (E)-1-[4'-(2-alkylaminoethoxy)phenyl]-1-(3'-hydroxyphenyl)-2-phenylbut-1-enes of the general formula

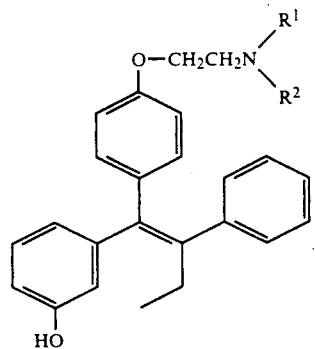

wherein $R^1$ and $R^2$ may be the same or different, provided that, when $R^1$ and $R^2$ are the same, each of them is a methyl or ethyl radical, and when $R^1$ and $R^2$ are different, one of them is hydrogen and the other is a methyl or ethyl radical, and the therapeutically compatible salts thereof, have a marked anti-estrogenic effect and are suitable for treating hormone-dependent mammary tumors.

The compounds can be prepared by dehydrating carbinols of the general formula

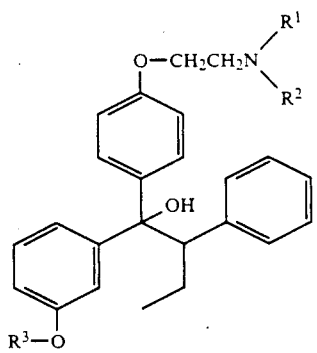

wherein $R^1$ and $R^2$ may be the same or different, provided that, when $R^1$ and $R^2$ are the same, each of them is a methyl or ethyl radical, and when $R^1$ and $R^2$ are different, one of them is a benzyl radical and the other is a methyl or ethyl radical; and wherein $R^3$ is hydrogen or an easily hydrolyzable protecting group, through the action of mineral acid while removing any protecting group present, isolating through crystallization the E-form from the pair of isomers obtained, and removing by hydrogenolysis any benzyl group present.

Compositions comprising the subject 1,1,2-triphenyl-but-1-ene derivatives are described also. The corresponding novel 1,1,2-triphenylbut-1-ene derivatives having the (Z) configuration are also disclosed.

17 Claims, No Drawings

1,1,2-TRIPHENYLBUT-1-ENE DERIVATIVES

This application is a continuation of application Ser. No. 06/930,015, filed Nov. 5, 1986, now abandoned, which is a continuation application of application Ser. No. 06/800,356, filed Nov. 21, 1985, now abandoned, which is a continuation application of application Ser. No. 06/328,723, filed Dec. 8, 1981, now abandoned.

FIELD OF THE INVENTION

The invention relates to novel 1,1,2-triphenylbut-1-ene derivatives having valuable therapeutic properties, and to compositions containing said derivatives. The compounds have a marked anti-estrogenic effect and are useful in the treatment of hormone-dependent mammary tumors.

BACKGROUND ART

Compounds having this basic structure and a dialkylaminoalkoxy radical in para position to one of the phenyl radicals on the C-atom 1 of the but-1-ene chain are already described in British Patent Specification No. 1,013,907. One of them, the (Z)-1-[4'-(2-dimethylaminoethoxy)phenyl]-1,2-diphenylbut-1-ene (tamoxifen, INN rec.) is a specific estrogen antagonist. By virtue of its marked anti-estrogenic activity, this active ingredient has already proved successful in the therapy of hormone-dependent mammary.

German Offengsschrift No. 2 807 599 has disclosed that a metabolite of tamoxifen, the (Z)-1-[4'-(2-dimethylaminoethoxy)phenyl]-1-(4'-(2-hydroxyphenyl)-2-phenylbut-1-ene ("4-hydroxytamoxifen") has an antiestrogenic effect comparable to tamoxifen. As reflected by European application No. 0 002 097, this also applies to a series of 1-[4'-(2-alkylaminoalkoxy)phenyl]-1-(4'-hydroxyphenyl)-2-phenylbut-1-enes ("4-hydroxytamoxifen derivatives").

BRIEF SUMMARY OF THE INVENTION

It has now surprisingly been found that by moving the hydroxy group from position 4 to position 3, compounds are obtained whose E-forms are clearly superior to tamoxifen in respect of binding affinity to the estrogen receptor. By virtue of this high specific affinity to the estrogen receptor, the compounds of the present invention exhibit not only marked antiuterotrophic activity but also an inhibitory effect on mammary tumors, which, as is shown by the example of compound 1 hereibelow, is above the activity of tamoxifen. 1,1,2-Triphenylbut-1-ene derivatives of the general formula (1) below, whose configuration preferably corresponds to the E-form, their preparation, their use and compositions containing same, comprise the subject matter of the present invention.

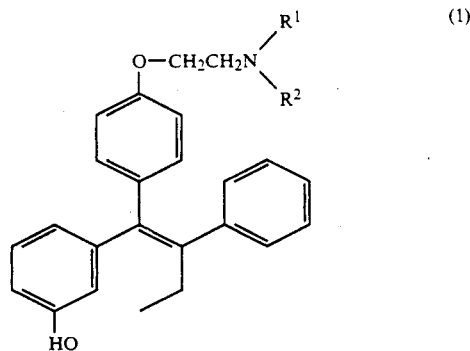

In formula (1), $R^1$ and $R^2$ may be the same or different, provided that, when $R^1$ and $R^2$ are the same, each of them is a methyl or ethyl radical, and when $R^1$ and $R^2$ are different, one of them is hydrogen and the other is a methyl or ethyl radical Specific compounds encompassed by formula (1) are as follows:

TABLE 1

| Compound No. | $R^1$ | $R^2$ | M.P. | Example |
|---|---|---|---|---|
| 1 | $CH_3$ | $CH_3$ | 162 to 163° C. | 1 h |
| 2 | $C_2H_5$ | $C_2H_5$ | 121° C. | 2 a |
| 3 | $CH_3$ | H | 125 to 127° C. | 3 |
| 4 | $C_2H_5$ | H | 174 to 175° C. | 4 |

DETAILED DESCRIPTION OF THE INVENTION

In this specification, the designations E and Z-forms relate to the position of the 3-hydroxyphenyl group (priority 1) on the C-atom 1 with respect to the position of the unsubstituted phenyl group (priority 1) on the C-atom 2 of the double bond [nomenclature rule: R. T. Morrison, R. N. Boyd, Lehrbuch der Organischen Chemie, Verlag Chemie, p. 167 (1974)].

The E and Z-forms are clearly distinguished by the resonance signals of the protons in the alkylamino group and in the —O—$CH_2$—group of the —$OCH_2CH_2NR^1R^2$ side-chain. In the instant compounds, the signals of the E-form occur at higher field than those of the Z-form [D. J. Collins, J. J. Hobbs and C. W. Emmers, J. Med. Chem., 14, 952 (1971)].

Characteristic distinguishing features of the novel E and Z-forms of 1-['-(2-dialkylaminoethoxy)phenyl]-1-(3'-hydroxyphenyl)-2-phenylbut-1-ene compounds are indicated in Table 2 below.

TABLE 2

| $R^1 = R^2$ | Isomer | M.P. | $^1$H-NMR Signals (δ, ppm) | |
|---|---|---|---|---|
| methyl (Example 1 h) | E-form | 162 to 163° C. | N(C$\underline{H}_3$)$_2$<br>OC$\underline{H}_2$ | 2.17<br>3.88 |
| methyl (Example 1 i) | Z-form | 173° C. | N(C$\underline{H}_3$)$_2$<br>OC$\underline{H}_2$ | 2.23<br>4.05 |
| ethyl (Example 2 a) | E-form | 121° C. | N(C$\underline{H}_2$C$\underline{H}_3$)$_2$<br>OC$\underline{H}_2$ | 0.97<br>3.90 |
| ethyl (Example 2 b) | Z-form | 156° C. | N(C$\underline{H}_2$C$\underline{H}_3$)$_2$<br>OC$\underline{H}_2$ | 1.01<br>4.03 |

The present invention further provides a method of preparing compounds of the general formula (1), which comprises dehydrating carbinols of the general formula (2)

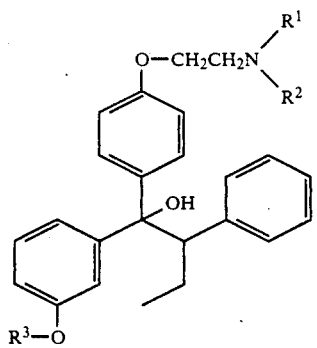

wherein $R^1$ and $R^2$ may be the same or different, provided that, when $R^1$ and $R^2$ are the same, each of them is a methyl or ethyl radical, and when $R^1$ and $R^2$ are different, one of them is a benzyl radical and the other is a methyl or ethyl radical; and wherein $R^3$ is hydrogen or an easily hydrolyzable protecting group, in a manner known per se, through the action of mineral acid, optionally with removal of the protecting group, isolating by crystallization the E-form from the pair of isomers obtained and removing any benzyl group present by hydrogenolysis. The tetrahydropyranyl group is preferred as an easily hydrolyzable protecting group. The removal of the protecting group and dehydration is achieved with mineral acid in an alcoholic medium, preferably in hydrochloric ethanolic solution. The isolation of the E-form by crystallization can be performed both with the acid-addition salts and with the free bases. Any benzyl group removal can be performed selectively by hydrogenolysis at room temperature with palladium-on-carbon.

By way of illustration, the compounds of the invention can be prepared as follows:

The starting compound of formula (3)

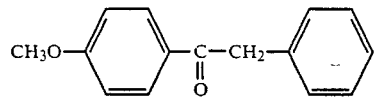

can be obtained by Friedel-Crafts reaction of methoxybenzene with phenylacetyl chloride. By reacting 1-(4'-methoxyphenyl)-2-phenylethan-1-one (3) with ethyl bromide in dimethylformamide and in the presence of sodium hydride, 1-(4'-methoxyphenyl)-2-phenyl-n-butan-1-one (4)

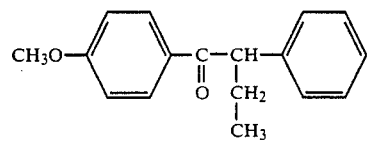

is obtained. An ether cleavage of (4) with pyridine hydrochloride leads to 1-(4'-hydroxyphenyl)-2-phenyl-n-butane-1-one (5)

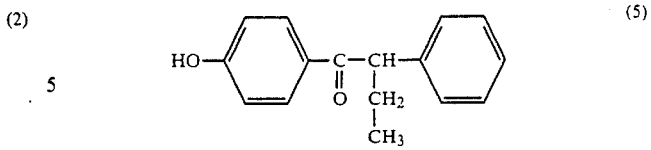

By reacting (5) with compounds of the general formula $R^1R^2N-CH_2CH_2Cl$ (6) wherein $R^1$ and $R^2$ may be the same or different, provided that, when $R^1$ and $R^2$ are the same, each of them is a methyl or ethyl radical, and when $R^1$ and $R^2$ are different, one of them is a benzyl radical and the other is a methyl or ethyl radical, compounds of the general formula (7)

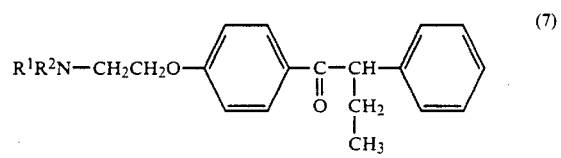

are obtained, wherein $R^1$ and $R^2$ are as defined in conjunction with formula (6) above. Compounds of the general formula (7) are then reacted with 3'-(2-tetrahydropyranyloxy)phenyl magnesium bromide to form the diastereomeric carbinols of the general formula (8)

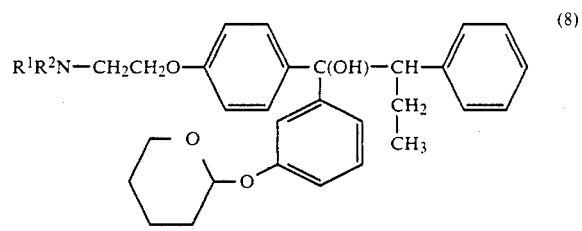

wherein $R^1$ and $R^2$ are as defined in conjunction with formulas (6) and (7). In the presence of mineral acid, compounds of the general formula (8) split off the tetrahydropyranyl group readily at room temperature and dehydrate under the influence of heat to form a pair of isomers, from which the E-isomer can be isolated by crystallization in both its salt and its base form, the benzyl radical of said E-isomer being removed by hydrogenolysis in the event that any benzyl radical is present, to give compounds of the general formula (1) hereinabove.

Equivalent to the compounds of formula (1) for the purposes of the present invention are the therapeutically compatible salts thereof. Such salts are typically the corresponding acid addition salts formed, for example, from non-toxic, pharmaceutically acceptable inorganic or organic acids, e.g. by conventional chemical methods. Such acid addition salts include, for example, those derived from inorganic acids such as hydrochloric, hydrobromic, sulfuric, sulfamic, phosphoric, nitric and the like; and those prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, fumaric, toluenesulfonic, and the like.

In the tests conducted, the compounds of the present invention have been found to have a high, therapeutically useful, anti-estrogenic effect.

The determination of the binding affinity to the estradiol receptor was made using rabbit uterus cytosol. In comparison to tamoxifen, the claimed compounds exhibited approximately ten times higher binding affinity.

The anti-uterotrophic effect was not measured, as is customary, after prepuberal female rats had been treated with active ingredient for three days (Dorfman test). A hormonal counter-regulatory reaction is not to be expected of prepuberal animals within this short treatment time and therefore nothing definite can be said about the anti-estrogenic properties of the active ingredient administered. For this reason, puberal female rats were subjected to treatment with active ingredient for three weeks. In this test, the claimed compounds exhibited a marked antiuterotrophic effect, partly above the activity of tamoxifen.

To measure the inhibitory effect on the mammary tumor, compound 1 ("3-hydroxytamoxifen") was selected from the instant substances and compared with tamoxifen under the same test conditions. The claimed compound proved to be clearly superior to tamoxifen in the inhibitory activity on the tumor.

The compounds according to the invention are thus a valuable contribution to the store of pharmaceutical preparations and can above all be used for treating mammals having malignant mammary tumors.

The present invention moreover relates to compositions comprising a compound of the general formula (1) or therapeutically compatible salt thereof as active ingredient and a nontoxic pharmaceutically acceptable carrier therefor, e.g. one or more of the conventional pharmaceutical carriers and adjuvants. The active ingredient is present in an effective amount (an antiestrogenically effective amount, an antiuterotrophically effective amount, or a tumor-inhibiting effective amount).

The claimed compounds are preferably administered orally. As a rule, the daily oral dose is 0.01 to 0.2 g., preferably 0.02 to 0.1 g., for a mammal weighing approximately 70 kg. Nevertheless, it may be necessary to depart from said amounts, depending on the individual response to the medicament, the nature of its formulation and the time or interval at which it is administered. Thus, in some cases it may be sufficient to manage with less than the above-mentioned lower amount, while in other cases the upper limit mentioned above has to be exceeded. If larger quantities are administered, it may be advisable to divide them into several single doses spread over the day.

The active ingredients can be processed for oral administration in conventional form, e.g. as capsules, tablets or dragees. By mixture with solid, powdery carriers, such as potato starch or corn starch, with additives such as sodium citrate or calcium carbonate and binding agents such as polyvinyl pyrrolidone, gelatin or cellulose derivatives, optionally with the addition of lubricating agents such as magnesium stearate, sodium lauryl sulfate or polyethylene glycols, they can be processed into tablets or dragee cores. Naturally, for the forms of oral administration, masking flavoring may be added.

Further suitable forms of administration are telescopically joinable capsules made, for instance, of hard gelatin, as well as closed soft gelatin capsules containing a softening agent, e.g. glycerin. The telescopically joinable capsules contain the active ingredient preferably as granules, e.g. mixed with fillers such as lactose, saccharose, mannitol, starches such as potato starch or amylopectin, cellulose derivatives or highly disperse silicic acids. In soft gelatin capsules, the active ingredient is preferably dissolved or suspended in suitable liquids, e.g. in plant oils or liquid polyethylene glycols.

Without further elaboration, it is believed that one of ordinary skill in the art can, using the preceding description, practice the present invention to its fullest extent. Therefore, the following examples are to be construed as merely illustrative and not limitative of the remainder of the specification and claims in any way whatsoever.

EXAMPLE 1

1-[4'-Dimethylaminoethoxy)phenyl]-1-(3'-hydroxyphenyl)-2-phenylbut-1-ene

Preparation of the Precursors a) 1-(4'-Methoxyphenyl)-2-phenylethan-1-one

To 10.8 g (0.10 mole) methoxybenzene and 13.9 g. (0.09 mole) phenylacetyl chloride in 1.0 l. methylene chloride there are added, by small amounts, 13.3 g. (0.10 mole) aluminium chloride at room temperature and with strong agitation. The reaction mixture is agitated for a further 2 hours and then is poured onto ice and 50 ml. hydrochloric acid are added. After separation of the organic phase, the aqueous solution is shaken out twice with 500 ml. methylene chloride each time, the combined organic phases are washed with water and the solvent is removed in vacuo. The smeary residue is freed of the volatile components by steam distillation and the remaining solid is crystallized from ethanol after filtration and washing with water. Obtained are colorless crystals having a melting point of 75° C.; $R_f$ 0.7 [CHCl$_3$/CH$_3$OH (9/1)]; yield: 18.3 g. (90%).

$C_{15}H_{14}O_2$ (226.2)

| $^1$H-NMR spectrum* (CDCl$_3$): | 3.77 s (3) OC$\underline{H}_3$ |
|---|---|
| | 4.18 s (2) C$\underline{H}_2$ |
| | 6.87 d (2) aromatic H [J = 9.0] |
| | 7.2 s (5) aromatic H |
| | 7.97 d (2) aromatic H [J = 9.0] |

*taken at 60 MHz; chemical shifts quoted in ppm using TMS as standard ($\delta$ = 0.0); relative intensities added in parentheses; s = singlet; d = doublet; t = triplet; m = multiplet; J = coupling constant in Hz.

b) 1-(4'-Methoxyphenyl)-2-phenyl-n-butan-1-one 2.4 G. (0.10 mole) sodium hydride are suspended in 300 ml. nitrogen-saturated, anhydrous dimethylformamide and after the slow addition of 22.6 g. (0.10 mole) 1-(4'-methoxyphenyl)-2-phenylethan-1-one in 50 ml. anhydrous dimethylformamide, are agitated for a further hour at 40° C. Then 13.1 g (0.12 mole) ethyl bromide in 50 ml. anhydrous dimethylformamide are added dropwise at 30° C. with agitation for a further 2 hours. To the reaction mixture is added 100 ml. water, and the resultant mixture is then shaken out twice with 250 ml. ether each time and the collected ether phases are carefully washed with water. After drying over sodium sulfate, the ether is removed in vacuo and the residue is crystallized from ethanol. Obtained are colorless crystals having a melting point of 44° C.; $R_f$ 0.55 (CH$_2$Cl$_2$); yield: 24.7 g. (97%).

$C_{17}H_{18}O_2$ (254.3)

| $^1$H-NMR spectrum (CDCl$_3$): | 0.87 | t (3) C$\underline{H}_3$ [J = 7.0] |
|---|---|---|
| | 1.50 to 2.53 | m (2) C$\underline{H}_2$ |
| | 3.70 | s (3) OC$\underline{H}_3$ |
| | 4.38 | t (1) C$\underline{H}$ [J = 7.2] |

| | | | |
|---|---|---|---|
| | 6.80 | d | (2) aromatic H [J = 9.0] |
| | 7.23 | s | (5) aromatic H |
| | 7.96 | d | (2) aromatic H [J = 9.0] | c) 1-(4'-Hydroxyphenyl)-2-phenyl-n-butan-1-one 25.4 G. (0.10 mole) 1-(4'-methoxyphenyl)-2-phenyl-n-butan-1-one and 34.5 g. (0.30 mole) pyridine hydrochloride are melted and refluxed at 220° C. for one hour while being agitated. The melt while still liquid is poured into ice water and the precipitate dissolved in 400 ml. ether. After washing the etheric solution with water, it is shaken out with 1 N sodium hydroxide solution. The aqueous alkaline solution is acidified with 5 N hydrochloric acid and extracted with 500 ml. ether. The organic phase is washed with water and dried over sodium sulfate. The solvent is removed in vacuo and the crude product is crystallized from dilute ethanol. Obtained are colorless crystals having a melting point of 131° C.; R$_f$0.45 [toluene/ethyl acetate (9/1)]; yield: 16.3 g. (68%).

$C_{16}H_{16}O_2$ (240.3)

| | | | | |
|---|---|---|---|---|
| $^1$H-NMR spectrum | 0.85 | t | (3) | CH$_3$ [J = 7.0] |
| (d$_6$ acetone): | 1.37 to 2.50 | m | (2) | CH$_2$ |
| | 2.73 to 3.47 | wide | (1) | OH [exchangeable with D$_2$O] |
| | 4.60 | t | (1) | CH [J = 7.6] |
| | 6.87 | d | (2) | aromatic H [J = 9.0] |
| | 7.33 | s | (5) | aromatic H |
| | 8.00 | d | (2) | aromatic H [J = 9.0] | d) 1-[4'-(2-Dimethylaminoethoxy)phenyl]-2-phenyl-n-butan-1-one 2.76 G. (0.12 mole) sodium are dissolved in 100 ml. anhydrous ethanol and 24 g. (0.19 mole) 1-(4'-hydroxyphenyl)-2-phenyl-n-butan-1-one are added. To the solution there are slowly added, at reflux temperature, 21.4 g (0.20 mole) dimethylaminoethyl chloride in 150 ml. toluene and the reaction mixture is refluxed for a further 8 hours. After cooling and separation of the insoluble components, the solvent is removed in vacuo and the residue is dissolved in 500 ml. ether. The etheric solution is shaken out several times with 2 N sodium hydroxide and then washed with water. After drying over sodium sulfate, the ether is removed in vacuo. There is obtained a colorless oil; R$_f$0.25 [CHCl$_3$/CH$_3$OH (9/1)]; yield 19.3 g. (62%).

$C_{20}H_{25}NO_2$ (311.4)

| | | | | |
|---|---|---|---|---|
| $^1$H-NMR spectrum | 0.88 | t | (3) | CH$_3$ [J = 7.0] |
| (CDCl$_3$): | 1.53 to 2.83 | m | (2) | CH$_2$ |
| | 2.28 | s | (6) | N(CH$_3$)$_2$ |
| | 2.67 | t | (2) | NCH$_2$ [J = 6.0] |
| | 4.03 | t | (2) | OCH$_2$ [J = 6.0] |
| | 4.40 | t | (1) | CH [J = 7.6] |
| | 6.87 | d | (2) | aromatic H [J = 8.4] |
| | 7.23 | s | (5) | aromatic H |
| | 7.97 | d | (2) | aromatic H [J = 8.4] | e) 1-[4'-(2Dimethylaminoethoxy)phenyl]-2-phenyl-1-[3'-(2-tetrahydropyranyloxy)phenyl]-n-butan-1-ol[diastereomers]

To 42.2 9. (0.15 mole) 3'-(2-tetrahydropyranyloxy)phenylmagnesium bromide in 200 ml. anhydrous tetrahydrofuran are carefully added 31.1 g. (0.10 mole) 1-[4'-(2-dimethylaminoethoxy)phenyl]-2-phenyl-n-butan-1-one in 100 ml. anhydrous tetrahydrofuran, and the mixture is then refluxed for 2 hours. The cooled reaction solution is added to 150 ml. saturated, aqueous ammonium chloride solution and shaken out with 100 ml. ether. The organic phase is washed with water and, after drying over sodium sulfate, the solvent is removed in vacuo. The oily residue is freed of impurities by chromatography on a column of silica gel with chloroform-/methanol (9/1), and the pure diastereomeric fraction is crystallized from petroleum ether. There are thus obtained colorless crystals having a melting point of 56° C.; R$_f$0.50 [CHCl$_3$/CH$_3$OH (9/1)]; yield 29.9 g. (61%).

$C_{31}H_{39}NO_4$ (489.7) calculated C 76.04 H 8.03 N 2.86., found C 76.28 H 7.92 N 2.79

Mol. wt. 489 (determined by mass spectrometry)
IR spectrum (KBr): ν(O—H) 3600 to 3100 cm$^{-1}$

| | | | |
|---|---|---|---|
| $^1$H-NMR spectrum | 0.6 wide | t (3) CH$_3$ | |
| (d$_6$ DMSO): | 1.23 to 1.97 | m (8) CH$_2$ | |
| | 2.20 | s (6) N(CH$_3$)$_2$ | |
| | 2.37 to 2.77 | t (2) NCH$_2$ | |
| | 3.27 to 4.03 | m (6) CH, 2 × OCH$_2$, OH | |
| | 5.45 wide | s (1) OCH | |
| | 6.40 to 7.43 | m (13) aromatic H | | f) 1-[4'-(2-Dimethylaminoethoxy)phenyl]-1-(3'-hydroxyphenyl)-2-phenyl-n-butan-1-ol [diastereomers]

To 49.0 g. (0.1 mole) of the pure diastereomeric fraction of 1-[4'-(2-dimethylaminoethoxy)phenyl]-2-phenyl-1-[3'-(2-tetrahydropyranyloxy phenyl]-n-butan-1ol in 500 ml. ethyl acetate there are added, at room temperature, 200 ml. 1% aqueous hydrochloric acid and the mixture is strongly shaken The emulsion is neutralized with 5% aqueous ammonia solution and, after settling, the aqueous phase is separated. The organic phase is washed with water and, after drying over sodium sulfate, the solvent is removed in vacuo. The residue is crystallized from ether/petroleum ether (1/1). Obtained are colorless crystals of the diastereomeric mixture having a melting point of 59 to 60° C.; R$_f$ 0.35 [CHCl$_3$/CH$_3$OH (7/3)]; yield 36.5 g. (90%).

$C_{26}H_{31}NO_3$ (405.5) calculated C 77.01 H 7.70 N 3.45; found C 76.81 H 7.86 N 3.38

Mol. wt. 405 (determined by mass spectrometry)
IR spectrum (KBr) : ν(O—H) 3600 to 2400 cm$^{-1}$

| | | |
|---|---|---|
| $^1$H-NMR spectrum | 0.7 | t CH$_3$ [J = 7.8] |
| (d$_6$ acetone): | 0.87 | t CH$_3$ [J = 7.6] |
| | 1.43 | m CH$_2$ |
| | 2.23 | s N(CH$_3$)$_2$ |
| | 2.30 | s N(CH$_3$)$_2$ |
| | 2.37 to 2.87 | m NCH$_2$ |
| | 3.47 to 4.40 | m OCH$_2$, CH |
| | 6.20 to 7.73 | m aromatic H | g) Preparation according to the invention (E)
-1-[4'-(2-Dimethylaminoethoxy)phenyl]-1-(3'-hydroxy-phenyl)-2-phenylbut-1-ene Hydrochloride 40.5 G. (0.1 mole) of the diastereomeric mixture of 1-[4'-(2-dimethylaminoethoxy)phenyl]-1-(3'-hydroxyphenyl)2-phenyl-n-butan-1-ol in 500 ml. ethanol are added to 25 ml. concentrated hydrochloric acid and refluxed for 2 hours. Then the solvent is removed in vacuo and the residue is crystallized from methanol/ether (1/1). Obtained are colorless crystals having a melting point of 221° C. (dec.); $R_f$ 0.25 [CHCl$_3$/CH$_3$OH (7/3)]; yield 20.3 g. (48%).

$C_{26}H_{30}ClNO_2$ (423.9)

IR spectrum (KBr): $\nu$(O—H, ⊕NH) 3650 to 2600 cm$^{-1}$

| $^1$H-NMR spectrum (d$_4$-methanol): | 0.9 | t (3) | CH$_3$ [J = 6.0] |
|---|---|---|---|
| | 2.5 | q (2) CH$_2$ [J = 6.0] | |
| | 2.97 | s (6) | N(CH$_3$)$_2$ |
| | 3.5 | t (2) | NCH$_2$ [J = 5.0] |
| | 4.27 | t (2) | OCH$_2$ [J = 5.0] |
| | 6.53 to 7.30 | m (13) aromatic H | | h) Preparation according to the invention (E)-1-[4'-(2-Dimethylaminoethoxy)phenyl]-1-(3-hydroxyphenyl)-2-phenylbut-1-ene 42.4 G. (0.1 mole) (E)-1-[4'-(2-dimethylaminoethoxy)phenyl]-1-(3'-hydroxyphenyl)-2-phenylbut-1-ene hydrochloride are suspended in 200 ml. dilute ammonia solution and shaken out twice with 250 ml. ethyl acetate each time. The organic phase is washed neutral with water and, after drying over sodium sulfate, the solvent is removed in vacuo. The residue is crystallized from ether. Colorless crystals having a melting point of 162 to 163° C. are obtained; $R_f$ 0.40 [CHCl$_3$/CH$_3$OH (7/3)]; yield: 37.2 g. (96%).

$C_{26}H_{29}NO_2$ (387.5) calculated C 80.59 H 7.54 N 3.61; found C 80.50 H 7.60 N 3.55

Mol. wt. 387 (determined by mass spectrometry)
IR spectrum (KBr) : $\nu$(O—H) 3650 to 3100 cm$^{-1}$

| $^1$H-NMR spectrum (d$_6$-DMSO): | 0.83 | t (3) | CH$_3$ [J = 6.0] |
|---|---|---|---|
| | 2.17 | s (6) | N(CH$_3$)$_2$ |
| | 2.27 to 2.73 | m (4) | CH$_2$N, CH$_2$CH$_3$ |
| | 3.88 | t (2) | OCH$_2$ [J = 5.8] |
| | 6.40 to 7.37 | m (13) aromatic H | |
| | 9.37 | s (1) | OH [exchangeable with D$_2$O] | i)
(Z)-1-[4'-(2-Dimethylaminoethoxy)phenyl]-1-3'-hydroxyphenyl]-2-phenylbut-1-ene The residue of the mother liquor of the crystals from Example 1 g is suspended in 200 ml. dilute ammonia solution and shaken out twice with 250 ml. ethyl acetate each time. The organic phase is washed with water and, after drying over sodium sulfate, the solvent is removed in vacuo. The residue is crystallized several times from methanol/water (1/1). Colorless crystals having a melting point of 173 ° C. are obtained; $R_f$ 0.40 [CHCl$_3$/CH$_3$OH (7/3)]; yield: 7.7 g (20%).

$C_{26}H_{29}NO_2$ (387.5) calculated C 80.59 H 7.54 N 3.61; found C 80.41 H 7.53 N 3.56

Mol. wt. 387 (determined by mass spectrometry)
IR spectrum (KBr) : $\nu$(O—H) 3650 to 3100 cm$^{-1}$

| $^1$H-NMR spectrum (d$_6$-DMSO): | 0.85 | t (3) | CH$_3$ [J = 6.4] |
|---|---|---|---|
| | 2.23 | s (6) | N(CH$_3$)$_3$ |
| | 2.30 to 2.80 | m (4) | CH$_2$N, CH$_2$CH$_3$ |
| | 4.05 | t (2) | OCH$_2$ [J = 5.8] |
| | 6.10 to 7.33 | m (13) | aromatic H |
| | 9.03 | s (1) | OH [exchangeable with D$_2$O] |

EXAMPLE 2 a

Preparation according to the invention (E)-1-[4'-(2-Diethylaminoethoxy)phenyl]-1-(3'-hydroxyphenyl)-2-phenylbut-1-ene 51.8 G. (0.1 mole) of the pure diastereomeric fraction, prepared analogously to Example 1e, of 1-[4'-(2-diethylaminoethoxy)phenyl]-2-phenyl-1-[3-(2-tetrahydropyranyloxy)phenyl]-n-butane-1-ol [yellow oil; $R_f$ 0.65 CHCl$_3$/CH$_3$OH (9/1)]in 500 ml. ethanol are added to 25 ml. concentrated hydrochloric acid. The mixture is then refluxed for 2 hours and treated as described in Examples 1 g to 1 h. There are thus obtained colorless crystals having a melting point of 121° C. [CH$_3$OH/H$_2$O (1/1)]; $R_f$ 0.30 [CHCl$_3$/CH$_3$OH (7/3)]; yield 10.4 g. (25%).

$C_{28}H_{33}NO_2$ (415.6) calculated C 80.91 H 8.00 N 3.37; found C 81.06 H 8.07 N 3.28

Mol. wt. 415 (determined by mass spectrometry)
IR spectrum (KBr) : $\nu$(O—H) 3600 to 3100 cm$^{-1}$

| $^1$H-NMR spectrum (d$_6$-DMSO): | 0.87 wide | t (3) | CH$_3$ |
|---|---|---|---|
| | 0.97 | t (6) | N(CH$_2$CH$_3$)$_2$ [J = 7.0] |
| | 2.20 to 2.87 | m (8) | CH$_2$N(CH$_2$)$_2$, CH$_2$CH$_3$ |
| | 3.90 | t (2) | OCH$_2$ [J = 7.0] |
| | 6.27 to 7.37 | m (13) | aromatic H |
| | 9.20 wide | s (1) | OH [exchangeable with D$_2$O] |

EXAMPLE 2 b

Z-1-[4'-Diethylaminoethoxy)phenyl]-1-(3'-hydroxyphenyl)-2-phenylbut-1-ene

Obtained in analogous fashio to the product of Example 1 i are colorless crystals having a melting point of 156° C. [methanol/water (1/1)]; $R_f$ 0.30 [CHCL$_3$/CH$_3$OH (7/3)]

$C_{28}H_{33}NO_2$ (415.6) calculated C 80.91 H 8.00 N 3.37; found C 80.78 H 8.00 N 3.26

Mol. wt. 415 (determined by mass spectrometry)
IR spectrum (KBr) : $\nu$(O—H) 3600 to 3100 cm$^{-1}$

| $^1$H-NMR spectrum (d$_6$-DMSO): | 0.90 wide | t | (3) | CH$_3$ |
|---|---|---|---|---|
| | 1.01 | t | (6) | N(CH$_2$CH$_3$)$_2$ [J = 7.0] |
| | 2.17 to 3.00 | m | (8) | CH$_2$N(CH$_2$), CH$_2$CH$_3$ |
| | 4.03 | t | (2) | OCH$_2$ [J = 7.0] |
| | 6.17 to 7.33 | | (13) | aromatic H |
| | 8.87 wide | s | (1) | OH [exchangeable with D$_2$O] |

Utilizing the appropriate starting materials and following the general procedures detailed hereinabove, the following additional compounds of the invention are obtained:

EXAMPLE 3

(E)-1-(3'-Hydroxyphenyl)-1-[4'-(2-methylaminoethoxy)phenyl]-2-phenylbut-1-ene

The product is obtained as colorless crystals having a melting point of 125° to 127° C. (ethanol); $R_f$ 0.15 [$CHCl_3/CH_3OH$ (7/3)].

$C_{25}H_{27}NO_2$ (373.5) calculated C 80.40 H 7.29 N 3.45, found C 80.55 H 7.32 N 3.61

Mol. wt. 373 (determined by mass spectrometry)

IR spectrum (KBr) : $\nu$(O—H; N—H) 3600 to 2300 $cm^{-1}$;

| $^1$H-NMR spectrum ($d_6$-DMSO): | 0.83 | t (3) C$\underline{H}_3$ [J = 7.0] |
|---|---|---|
| | 2.13 to 2.70 | m (2) C$\underline{H}_2$ |
| | 2.30 | s (3) NC$\underline{H}_3$ |
| | 2.73 | t (2) NC$\underline{H}_3$ [J = 5.6] |
| | 3.83 | t (2) OC$\underline{H}_2$ [J = 5.6] |
| | 6.40 to 7.43 | m (13) aromatic H |

EXAMPLE 4

(E)-1-[4'-Ethylaminoethoxy)phenyl]-1-(3'-hydroxyphenyl)-2-phenylbut-1-ene

The product is obtained as colorless cyrstals having a melting point of 174° to 175° C. (acetone); $R_f$ 0.15 [$CHCl_3/CH_3OH$ (7/3)].

$C_{26}H_{29}NO_2$(387.5) calculated C 80.59 H 7.54 N 3.61; found C 80.55 H 7.58 N 3.67

Mol. wt. 387 (determined by mass spectrometry)

IR spectrum (KBr) : $\nu$(O—H) 3600 to 3100 $cm^{-1}$

| $^1$H-NMR spectrum: ($d_6$-DMSO) | 0.85 | t (3) | C$\underline{H}_3$ [J = 7.0] |
|---|---|---|---|
| | 0.98 | t (3) | C$\underline{H}_3$ [J = 7.2] |
| | 2.13 to 2.73 | m (4) | NC$\underline{H}_2$CH$_3$, C$\underline{H}_2$CH$_3$ |
| | 2.80 | t (2) | NC$\underline{H}_2$ [J = 5.6] |
| | 3.90 | t (2) | OC$\underline{H}_2$ [J = 5.6] |
| | 6.43 to 7.43 | m (13) | aromatic H |

EXAMPLE 5

A pharmaceutical preparation containing (E)-1-[4'-(2-dimethylaminoethoxy)phenyl]-1-(3'-hydroxyphenyl)-2-phenylbut-1-ene hydrochloride 21.88 G. powdered (E)-1-[4'-(2-dimethylaminoethoxy)phenyl]-1-ene -(3'-hydroxyphenyl)-2-phenylbut-1-ene hydrochloride are mixed with 40 g. lactose and 140 g. starch. There are then added 33 g. talcum and 13 g. calcium stearate. After having been carefully mixed, the resultant mixture is filled into two thousand hard gelatin capsules of a suitable size, each containing 10 mg. active ingredient (calculated as free base).

EXAMPLE 6

A pharmaceutical preparation containing (E)-1-[4-(2-ethylaminoethoxy)phenyl]-1-(3'-hydroxyphenyl)-2-phenylbut-1-ene After having been mixed with 111 g. mannitol, 15 g. corn starch and 6 g. alginic acid, 20.0 g. finely powdered . (E)-1-[4'-(2-ethylaminoethoxy)phenyl]-1(3'-hydroxyphenyl)-2-phenylbut-1-ene are granulated and the dried granules, after having been carefully mixed with 0.75 g. methyl cellulose and 1.5 g. magnesium stearate, are compressed into one thousand tablets, each containing 20 mg. active ingredient.

Pharmacological Tests a) Binding Affinity to the Estradiol Receptor

The binding affinity to the estradiol receptor was measured according to the method of N. Devleeschouwer, G. Leclercq, A. Danguy and J.C. Heuson [Europ. J. Cancer, 14, 721–723 (1978)]. The uterus cytosol of female, prepuberal white rabbits of 2 kg. weight (New Zealand rabbits) was incubated for 18 hours at 4° C. with $2.5 \times 10^{-9}$M[$^3$H]-estradiol as well as with the addition of unlabelled estradiol (control) or test substance of different concentration. The binding affinity to the estradiol receptor is expressed by the concentration of unlabelled estradiol (control) or test substance which is added to the uterus cytosol and brings about a 50% replacement of the [$^3$H]-estradiol bound to the estradiol receptor.

TABLE 3

Binding Affinity of the Test Substances

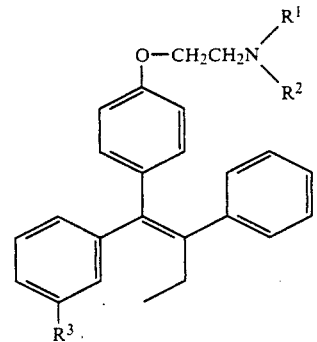

| Compound No. | $R^1$ | $R^2$ | $R^3$ | $ED_{50\%}{}^x$ [M] |
|---|---|---|---|---|
| Estradiol (control) | — | — | — | $1.3 \times 10^{-9}$ |
| Tamoxifen | $CH_3$ | $CH_3$ | H | $3.8 \times 10^{-7}$ |
| 1 | $CH_3$ | $CH_3$ | OH | $2.4 \times 10^{-8}$ |
| 2 | $C_2H_5$ | $C_2H_5$ | OH | $6.5 \times 10^{-8}$ |
| 3 | $CH_3$ | H | OH | $3.7 \times 10^{-8}$ |

$^x$Concentration of the substance which replaces 50% [$^3$H]-estradiol from the estradiol receptor.

b) Anti-uterotrophic Effect

The anti-uterotrophic effect was determined according to a modified "Dorfman Test" [R. I. Dorfman, Methods in Hormone Research II, p. 707, Academic Press, New York - London, 1962]on puberal, female Sprague-Dawley rats.

The test compounds were put in 0.25% aqueous agar suspension and administered by stomach tube six times weekly over a period of 21 days. At the end of testing, the uterine weight of the animals treated with active ingredient was related to the uterine weight of the control animals which only received a blank agar suspension.

TABLE 4

Anti-uterotrophic Activity of the Test Substances

| Compound No. | No. of Test Animals | Dose mg./kg./day | Uterine Weight compared to Control Animals |
|---|---|---|---|
| Tamoxifen | 10 | 3 | −40% |
| 1 | 10 | 3 | −42% |
| 2 | 10 | 3 | −39% |

TABLE 4-continued

| | Anti-uterotrophic Activity of the Test Substances | | |
|---|---|---|---|
| Compound No. | No. of Test Animals | Dose mg./kg./ day | Uterine Weight compared to Control Animals |
| 3 | 10 | 3 | −53% | c) Inhibitory Effect on the Mammary Tumor

The inhibitory effect on the tumor was determined on the model of the 7,12-dimethylbenz(a)anthraceneinduced mammary tumor of the female Sprague-Dawley rat (Hanover breed) according to the method of M.J. Golder [Europ. J. Cancer 11, 571 (1975)]and D. P. Griswold et al [Cancer Research 26, 2169 (1966)].

The test compounds were put in 0.25% agar suspension and administered by stomach tube six times weekly over a period of 28 days. Twice weekly and on the 28th day of testing the number of animals was determined and the tumor surface (mm²/animal) of the therapy animals and control animals was measured. At the end of testing, the percentage increase of the average tumor surface of the treated animals was determined in comparison to the control animals, the surface of the latter being taken as 100%.

TABLE 5

| | Inhibitory Activity of the Test Substances on the Tumor | | |
|---|---|---|---|
| Compound No. | No. of Test Animals | Dose mg./kg./ Day | Relative Increase of the Average Tumor Surface |
| Blank Control | 10 | — | 100% |
| Tamoxifen | 12 | 3 | 35% |
| 1 | 12 | 3 | 23% |

From the foregoing description, one of ordinary skill in the art can readily ascertain the essential characteristics of the present invention and, without departing from the spirit and scope thereof, can make various changes in and/or modifications of the invention to adapt it to various usages and conditions. As such, these changes and/or modifications are properly, equitably and intended to be within the full range of equivalence of the following claims.

What we claim is:

1. A compound of the formula 1

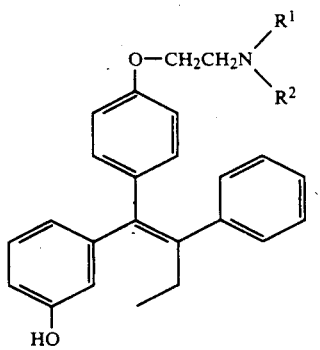

(1)

having the E configuraiton wherein R¹ and R² may be the same or different, provided that, when R¹ and R² are the same, each of them is a methyl or ethyl radical, and when R¹ and R² are different, one of them is hydrogen and the other is a methyl or ethyl radical; or a non-toxic, pharmaceutically acceptable salt thereof.

2. The compound (E)-1-[4'(2-dimethylaminoethoxy)-phenyl]-1-(3'-hydroxyphenyl)-b 2phenylbut-1-ene or a non-toxic, pharmaceutically acceptable salt thereof.

3. The compound of claim 1 which is (E)-1-[4'-(2-dimethylaminoethoxy)phenyl]-1-(3'-hydroxyphenyl)-2-phenylbut-1-ene.

4. The compound (E)-1-[4'(2-diethylaminoethoxy)-phenyl]-1-(3'-hydroxyphenyl)-2-phenylbut-1-ene or a non-toxic, pharmaceutically acceptable salt thereof.

5. The compound of claim 1 which is (E)-1-[4'-(2-diethylaminoethoxy)phenyl]-1-(3'-hydroxyphenyl) 2-phenylbut-1-ene.

6. The compound (E)-1-(3'-hydroxyphenyl)-1-[4'-(2-methylaminoethoxy)phenyl]-2-phenylbut-1 -ene or a non-toxic, pharmaceutically acceptable salt thereof.

7. The compound of claim 1 which is (E)-1(3'-hydroxyphenyl)-1-[4'-(2-methylaminoethoxy)phenyl]-2-phenylbut-1-ene.

8. The compound (E)-1-[4-ethylaminoethoxy)-phenyl]-1-(3'-hydroxyphenyl)-2-phenylbut-1-ene or a non-toxic, pharmaceutically acceptable salt thereof.

9. The compound of claim 1 which is (E)-1-[4'-ethylaminoethoxy)phenyl]-1-)3'-hydroxyphenyl)-2phenylbut-1-ene.

10. A composition of matter comprising an antiestrogenically effective amount of or a tumor-inhibiting effective amount of a compound or salt as claimed in claim 1, and a non-toxic, pharmaceutically acceptable carrier therefor.

11. A composition of matter comprising an anti-estrogenically effective amount or a tumor-inhibiting effective amount of (E)-1-[4'-(2-dimethylaminoethoxy) phenyl]-1-(3'-hydroxyphenyl)-(2-phenylbut-1-ene or pharmaceutically acceptable salt thereof and a non-toxic, pharmaceutically acceptable carrier therefor.

12. A method for eliciting an anti-estrogenic response in a mammal which comprises administering to said mammal an anti-estrogenically effective amount of a compound or salt as claimed in claim 1.

13. A method of treating a mammal having a mammary tumor which comprises administering to said mammal a mammary tumor-inhibiting effective amount of a compound or salt as claimed in claim 1.

14. A method for eliciting an anti-estrogenic response in a mammal which comprises administering to said mammal an anti-estrogenically effective amount of a composition as claimed in claim 10.

15. A method of treating a mammal having a mammary tumor which comprises administering to said mammal a mammary tumor-inhibiting effective amount of a composition as claimed in claim 10.

16. A method for eliciting an anti-estrogenic response in a mammal which comprises administering to said mammal an anti-estrogenically effective amount of (E) -1-[4'-(2-dimethylaminoethoxy) phenyl]-1-(3'-hydroxyphenyl)-2phenylbut-1-ene or pharmaceutically acceptable salt thereof.

17. A method of treating a mammal having a mammary tumor which comprises administering to said mammal a mammary tumor inhibiting effective amount of (E)-1-[4'-(2-dimethylaminoethoxy) phenyl]-1-(3'-hydroxyphenyl)-2phenylbut-1-ene or pharmaceutically acceptable salt thereof.

* * * * *